US011556940B2

(12) United States Patent
Sodhi et al.

(10) Patent No.: US 11,556,940 B2
(45) Date of Patent: Jan. 17, 2023

(54) TASTE PROFILE SYSTEM

(71) Applicant: International Business Machines Corporation, Armonk, NY (US)

(72) Inventors: Manjit Singh Sodhi, Bangalore (IN); Raghuveer Prasad Nagar, Kota (IN); Satyam Jakkula, Bengaluru (IN)

(73) Assignee: International Business Machines Corporation, Armonk, NY (US)

( * ) Notice: Subject to any disclaimer, the term of this patent is extended or adjusted under 35 U.S.C. 154(b) by 354 days.

(21) Appl. No.: 16/688,275

(22) Filed: Nov. 19, 2019

(65) Prior Publication Data
US 2021/0150543 A1   May 20, 2021

(51) Int. Cl.
| | |
|---|---|
| G06Q 30/02 | (2012.01) |
| G06Q 50/12 | (2012.01) |
| G06Q 30/06 | (2012.01) |
| G06Q 50/22 | (2018.01) |
| G16H 20/60 | (2018.01) |
| G06Q 10/10 | (2012.01) |
| G09B 19/00 | (2006.01) |

(52) U.S. Cl.
CPC ............ *G06Q 30/02* (2013.01); *G06Q 10/10* (2013.01); *G06Q 30/0631* (2013.01); *G06Q 50/12* (2013.01); *G06Q 50/22* (2013.01); *G09B 19/0092* (2013.01); *G16H 20/60* (2018.01)

(58) Field of Classification Search
None
See application file for complete search history.

(56) References Cited

U.S. PATENT DOCUMENTS

| | | | |
|---|---|---|---|
| 6,236,974 B1* | 5/2001 | Kolawa | G06Q 30/02 |
| | | | 705/7.32 |
| 8,504,440 B1 | 8/2013 | Kolawa et al. | |
| 2006/0199155 A1 | 9/2006 | Mosher | |
| 2013/0191143 A1 | 7/2013 | Schwarzberg et al. | |
| 2014/0334691 A1* | 11/2014 | Cho | G06Q 30/0631 |
| | | | 382/110 |
| 2016/0012513 A1 | 1/2016 | Martinez et al. | |
| 2016/0350659 A1 | 12/2016 | Tsao | |
| 2016/0353235 A1 | 12/2016 | Williams et al. | |
| 2017/0063567 A1* | 3/2017 | Tanaka | H05B 6/668 |
| 2018/0157232 A1* | 6/2018 | Chen | A47J 36/00 |
| 2018/0341979 A1* | 11/2018 | Byron | G06Q 30/0277 |
| 2019/0130448 A1 | 5/2019 | Kairinos | |

(Continued)

OTHER PUBLICATIONS

Mell et al., "The NIST Definition of Cloud Computing", Recommendations of the National Institute of Standards and Technology, Sep. 2011, 7 pages.

*Primary Examiner* — Scott A Zare
(74) *Attorney, Agent, or Firm* — Grant M. McNeilly (57) ABSTRACT

A method can include obtaining personal data of a user and generating, based at least in part on the personal data of the user, a taste profile of the user. The taste profile can include a set of food characteristics that corresponds to one or more food preferences of the user. The method can include obtaining contextual data that corresponds to a location of the user. The method can include generating, based at least in part on the taste profile and the contextual data, a food recommendation. The food recommendation can include a predicted food preference of the user. The method can include transmitting the food recommendation to the user.

20 Claims, 6 Drawing Sheets

(56) References Cited

U.S. PATENT DOCUMENTS

| | | | |
|---|---|---|---|
| 2019/0281878 A1* | 9/2019 | Tang | G06F 16/90324 |
| 2020/0159750 A1* | 5/2020 | Shadrokh | G06F 16/248 |
| 2020/0342977 A1* | 10/2020 | Son | G06Q 30/02 |
| 2020/0363778 A1* | 11/2020 | Mahapatra | H05B 6/6464 |

* cited by examiner

TASTE PROFILE SYSTEM

BACKGROUND

The present disclosure relates to dining options, and more specifically, to dining recommendations.

Computer-implemented methods can assist users with selecting foods based on aspects such as diet plans, medical treatment, previous food purchases, and proximity to restaurants. Some computer-implemented methods can incentivize a user to purchase food items based on a determined likelihood that the user will purchase the food items.

SUMMARY

According to embodiments of the present disclosure, a method can include obtaining personal data of a user. The method can further include generating, based at least in part on the personal data of the user, a taste profile of the user. The taste profile can comprise a set of food characteristics. The set of food characteristics can correspond to one or more food preferences of the user. The method can further include obtaining contextual data that corresponds to a location of the user. The method can further include generating, based at least in part on the taste profile and the contextual data, a food recommendation. The food recommendation can include a predicted food preference of the user. The method can further include transmitting the food recommendation to the user.

A system and a computer program product corresponding to the above method are also included herein.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Aspects of the present disclosure relate to dining recommendations; more particular aspects of the present disclosure relate to a taste profile system. While the present disclosure is not necessarily limited to such applications, various aspects of the disclosure may be appreciated through a discussion of various examples using this context.

Computer-implemented tools can assist users with making dining selections. For example, in some instances, a computer-implemented tool can utilize information such as a user's location and purchase history to predict dining options that may interest the user. In some instances, a computer-implemented tool can generate an incentive, such as an advertised discount, to purchase a food item based on a likelihood that a user will purchase the food item. While such tools can be helpful, they can be limited in their ability to assess a user's food preferences and/or needs.

To address these and other challenges, embodiments of the present disclosure include a system and method for generating a taste profile for a user. A taste profile can include a set of food items and/or a set of food characteristics that correspond to one or more food preferences of a user. Embodiments of the present disclosure can further generate, based at least in part on the taste profile, a food recommendation that can correspond to a food preference of the user.

Figure 1:
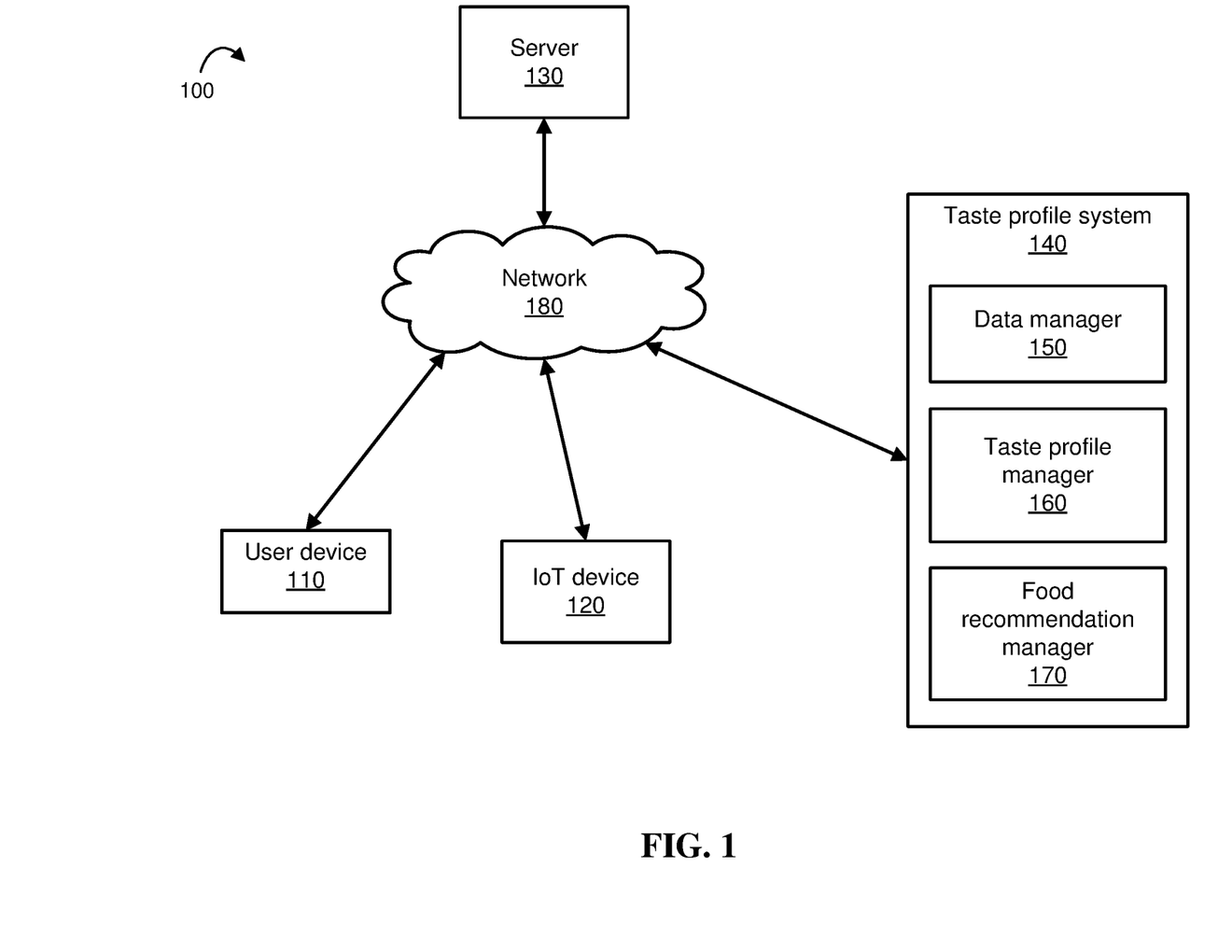
FIG. 1 depicts an example computing environment that includes a taste profile system, in accordance with embodiments of the present disclosure.

Turning to the figures, FIG. 1 illustrates an example computing environment 100 that can include a taste profile system 140 and at least one of each of a user device 110, an Internet of Things ("IoT") device 120, a server 130, and a network 180. In some embodiments, the taste profile system 140 and the at least one user device 110, IoT device 120, and server 130 can exchange data with one another through the at least one network 180. In some embodiments, each of the taste profile system 140 and the at least one user device 110, IoT device 120, server 130, and network 180 can include a computer system, such as the computer system 401 described with respect to FIG. 4.

Figure 2:
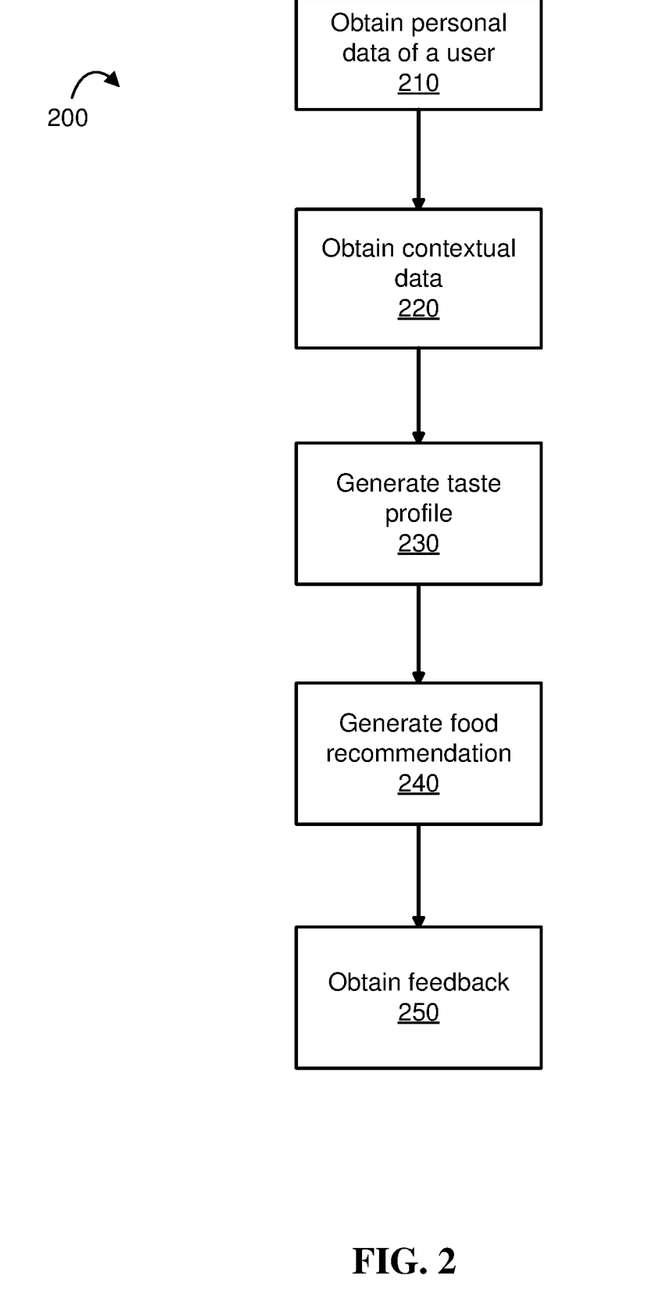
FIG. 2 depicts a flowchart of an example method for generating a food recommendation, in accordance with embodiments of the present disclosure.

Referring back to FIG. 1, the taste profile system 140 can include one or more processors (see, e.g., processor 410, FIG. 4) configured to perform one or more of the method steps described with respect to FIG. 2. For example, each of the data manager 150, taste profile manager 160, and food recommendation manager 170 can include one or more processors having programming instructions to perform one or more of the method steps described with respect to FIG. 2. Particularly, in some embodiments, the data manager 150 can perform steps 210 and 220; the taste profile manager 160 can perform step 230; and the food recommendation manager 170 can perform steps 240 and 250 of the method 200 described with respect to FIG. 2. In some embodiments, the taste profile system 140 can include a trained machine learning module, such as the trained machine learning module 360 described with respect to FIG. 3.

Referring back to FIG. 1, in some embodiments, the taste profile system 140 can be included in a discrete computer system located remotely from the user device 110, the IoT device 120, and the server 130. In some embodiments, the taste profile system 140 can be integrated into the server 130 and/or the user device 110.

In some embodiments, the user device 110 can include a mobile phone, smart watch, tablet, computer, etc. The user device 110 can include a display configured to present graphical and/or alphanumeric messages from the taste profile system 140. The user device 110 can also include a user-input interface, such as a touchscreen, keyboard, and/or microphone that allows a user to input oral or written feedback into the user device 110, which feedback can be transmitted to the taste profile system 140 through the network 180. In some embodiments, the user device 110 can include a location monitoring system, such as a global positioning system ("GPS"), configured to transmit a location of the user device 110 to the taste profile system 140. In some embodiments, the user device 110 can be configured to store personal data of a user and contextual data.

In some embodiments, the IoT device 120 can include devices and/or appliances configured to obtain information and transmit the information across a network, such as network 180. For example, in some embodiments, IoT device 120 can include a camera configured to transmit images across a network, an electronic personal assistant (e.g., a smart speaker configured to receive and execute verbal commands), and a smart refrigerator or smart container (e.g., a receptacle for storing food and/or food ingredients that is configured to monitor a type and/or quantity of food and/or food ingredients within the receptacle and transmit information corresponding to the type and/or quantity across a network).

In some embodiments, the server 130 can include one or more web servers configured to store and transmit data such as personal data of a user, contextual data, taste profiles, food recommendations, and/or user feedback.

In some embodiments, the network 180 can be a wide area network (WAN), a local area network (LAN), the Internet, or an intranet. In some embodiments, the network 180 can be substantially similar to, or the same as, cloud computing environment 50 described in FIG. 5.

FIG. 2 illustrates a flowchart of an example method 200 for generating a food recommendation, in accordance with embodiments of the present disclosure. The method 200 can be performed by a taste profile system, such as the taste profile system 140 described with respect to FIG. 1.

Referring back to FIG. 2, in step 210 the taste profile system can obtain personal data of a user. Personal data of a user can include information about the user and the user's activities. For example, in some embodiments, personal data of a user can include calendar data, such as dates that can be significant to the user (e.g., birthday, anniversary, etc.). In some embodiments, calendar data can include dates corresponding to events that the user has attended or will attend. The taste profile system can obtain such calendar data from a user device, such as the user device 110 discussed with respect to FIG. 1.

In some embodiments, personal data of a user can include information about the user's Internet activities, such as social media posts and searching or browsing history. In these embodiments, the taste profile system can obtain such Internet activity information from a user device, such as the user's mobile phone or computer, or from a web server configured to store information about the user's Internet activities. In some embodiments, personal data of a user can include information about the user's purchasing activity, such as foods and/or food ingredients that the user has purchased online, in grocery stores, and/or in restaurants. In these embodiments, the taste profile system can obtain such purchasing activity information from a user device, such as the user's mobile phone, or from a remote web server configured to store information about the user's purchasing activity. In some embodiments, personal data of a user can include data from IoT devices, such as camera images and/or audio recordings of a user preparing food in the user's kitchen, data about a quantity of food ingredients and/or food items from a smart container or a smart refrigerator, and information about commands issued by the user to an electronic assistant, such as a smart speaker. By obtaining the personal data of a user discussed above, the taste profile system can generate a taste profile that corresponds to an array of user activities, which can allow the taste profile system to generate accurate food recommendations, as discussed in further detail below.

In step 220, the taste profile system can obtain contextual data. In some embodiments, contextual data can include information regarding a time, date, or season (e.g., fall, winter, spring, or summer), a location, and/or weather conditions corresponding to a user's dining activity (e.g., ordering a carry-out food item, dining at a restaurant, preparing a home-cooked food item (e.g., preparing a food item at a residential location, such as a user's home), etc.). In some embodiments, contextual data can include food information, such as one or more available restaurant menus, that corresponds to the user's location. For example, in some embodiments, contextual data can include that the user is in San Diego, Calif., on a Saturday afternoon, as well as restaurant menus for five sushi restaurants that are within a 10 mile radius of the user's location. In another example, contextual data can include that the user is traveling toward the user's home in snowy weather at 6 PM.

In some embodiments, contextual data can be obtained from at least one of a user device, IoT device, and a web server, such as those discussed with respect to FIG. 1. In some embodiments, personal user data and/or contextual data can be input into the taste profile system by a user (e.g., in some embodiments, through a user-input interface, such as a touchscreen of a user device, a user can enter information such as the user's birthday or an upcoming event and transmit the information to the taste profile system). In some embodiments, personal user data and/or contextual data can include structured data and/or unstructured data.

In step 230, the taste profile system can generate a taste profile based, at least in part, on the personal data of a user obtained in step 210 and/or contextual data obtained in step 220. A taste profile can include a set of food items and/or a set of food characteristics that correspond to one or more food preferences of a user. In some embodiments, a food preference of a user can indicate a user's propensity to choose a food item for consumption. For example, in some embodiments, a taste profile can include food items (e.g., baked salmon, grilled chicken, lasagna, specific entrees from a restaurant menu, etc.) that the user would likely choose for consumption. In some embodiments, a taste profile can include food characteristics, such as categories of foods (e.g., breads, pastries, vegetables, produce, desserts, spicy foods, organic foods, gluten-free foods); food content (e.g., whether foods include particular food ingredients, such as butter, sugar, garlic, pepper, or cumin); food flavors (e.g., sweet, savory, sour, salty, bitter); and/or food sources (e.g., home-cooked, restaurant, grocery store) that correspond to food items that the user would likely choose for consumption.

In some embodiments, a taste profile can include one or more sets of preference scores that can quantify a likelihood that the user will choose a food item for consumption. In some embodiments, preference scores can correspond to food items. In some embodiments, preference scores can correspond to food characteristics included in the taste profile. In some embodiments, step 230 can include generating structured data from personal data of the user and/or contextual data that is unstructured.

For example, in some embodiments, a taste profile can include a table, such as TABLE 1 below.

TABLE 1

| Food | Category | Occasion | Source | Content | Score: Food | Score: Category |
|---|---|---|---|---|---|---|
| Steak | Meats | Birthday | Restaurant A | Garlic, pepper . . . | 8.5 | 9.0 |
| Potato soup | Soups | Rainy weather | Home-cooked | Potato, sour cream, chili powder . . . | 9.0 | 8.0 |
| Chicken salad | Salads | Lunch | Grocery store A | Romaine lettuce, pepper . . . | 7.5 | 5.5 |

TABLE 1 is an example tabular representation of a taste profile of a user. TABLE 1 includes a set of food items ("Food" column). TABLE 1 further includes food characteristics corresponding to the set of food items, such as a set of food categories ("Category" column), a set of relevant occasions ("Occasion" column), a source from which the food item was obtained ("Source" column), a list of food ingredients included in each food item ("Content" column), and preference scores generated by the taste profile system ("Score: Food" and "Score: Category" columns). TABLE 1 can be generated by a taste profile system based, at least in part, on the personal data of the user obtained in step 210 and/or contextual data obtained in step 220.

For example, in some embodiments, the user can consent to automatically sharing the user's social media posts and the user's purchase information with the taste profile system. Continuing with this example, the user can create a social media post indicating that the user visited Restaurant A and enjoyed a particular steak dish on the user's birthday. In this example, the taste profile system can obtain the social media post and implement natural language processing technology to identify the dish, the restaurant, the occasion (i.e., the user's birthday) and the fact that the user enjoyed the dish. Based on this information, the taste profile system can obtain a menu from a website for Restaurant A and identify food ingredients included in the dish. Continuing with this example, based on the user's language describing the dish, the taste profile system can assign the dish a preference score on a scale of 1 to 10, where a preference score of 10 represents a maximum level of preference for the dish by the user. Continuing with this example, the taste profile system can analyze the purchase history of the user, identify that the user frequently purchases meat foods, and assign a meat category preference score of 9 on a scale of 1 to 10. In this example, the preference score indicates that, based on the user's purchase history, the user would likely choose a meat food item for consumption among a selection of meat and non-meat food items.

Continuing with this example of the taste profile system generating the TABLE 1 taste profile, in some embodiments, the taste profile system can obtain images and/or sounds of the user preparing a dish. The images and/or sounds can be captured by the user's IoT camera located in the kitchen of the user's home. Continuing with this example, the captured images can include images of pages of a recipe book and food ingredients utilized by the user. Additionally, the captured sounds can include statements by the user regarding the recipe. Continuing with this example, the taste profile system can implement image analysis and/or audio analysis technologies to identify that the user is following a recipe to make potato soup. Additionally in this example, from a web server, the taste profile system can obtain the time, date, and rainy weather information that corresponds to the user's activity. Accordingly, the taste profile system can indicate in TABLE 1 that the user is preparing a home-cooked potato soup dish during rainy weather.

In some embodiments, one or more components of a taste profile, such as scores assigned to food items and/or food characteristics of food items, can be generated by a trained machine learning module, such as the trained machine learning module 360, described with respect to FIG. 3 below.

In step 240, the taste profile system can generate a food recommendation based, at least in part, on the taste profile and the contextual data. In some embodiments, a food recommendation can include a suggestion from the taste profile system that the user obtain a food item having particular food characteristics. For example, in some embodiments, a user can have a taste profile that includes high preference scores (e.g., preference scores greater than 7 on a scale of 1 to 10) for hot spices. In this example, the taste profile system can generate such a taste profile based on: (1) the user's frequent purchases of hot spices (the taste profile system can identify such purchases from purchase history data that the taste profile system obtains from the user's personal computer); (2) the user's regular use of hot spices when cooking at home (the taste profile system can identify such use from IoT camera images of the user preparing food in the user's home kitchen); and/or (3) the user's attendance at an exhibition of spicy foods (the taste profile system can identify such attendance from calendar entry information obtained from the user's mobile telephone).

Continuing with this example, the taste profile system can implement machine learning processes to assign a preference score of 8.5 to food items that include hot spices, such as red chili peppers. Continuing with this example, the user can visit a restaurant, and the taste profile system can obtain location information from the user's mobile telephone indicating that the user is at the restaurant. Continuing with this example, the taste profile system can obtain information about the dishes offered on the restaurant's menu from a web server. Continuing with this example, the taste profile system can compare the restaurant's menu information to the user's taste profile and identify a match (e.g., the restaurant's menu includes a dish made with red chili peppers; thus, both the taste profile and the restaurant's menu include red chili peppers). Continuing with this example, based on the comparison and the preference score, the taste profile system can predict that the user would likely choose the dish for consumption (i.e., the taste profile system can determine that the dish is a predicted food preference of the user). In response, the taste profile system can generate a food recommendation suggesting that the user purchase the dish, and the taste profile system can transmit the food recommendation to the user (e.g., the taste profile system can transmit an alphanumeric message recommending the dish to the user's mobile telephone, on which the user can view the alphanumeric message).

In some embodiments, method 200 can include the taste profile system obtaining feedback from a user in step 250. For example, in some embodiments, step 250 can include a user indicating to the taste profile system whether a generated food recommendation accurately predicted the user's food preference. In these embodiments, step 250 can be used to provide reinforcement learning to the taste profile system. For example, in some embodiments, the taste profile system can use the user feedback to adjust a trained machine learning module that it uses to generate a taste profile. In some embodiments, the taste profile system can use the user feedback to adjust a trained machine learning module that it uses to generate a food recommendation. By obtaining feedback from a user in step 250, embodiments of the present disclosure can improve the accuracy of subsequent food recommendations generated by the taste profile system.

Figure 3:
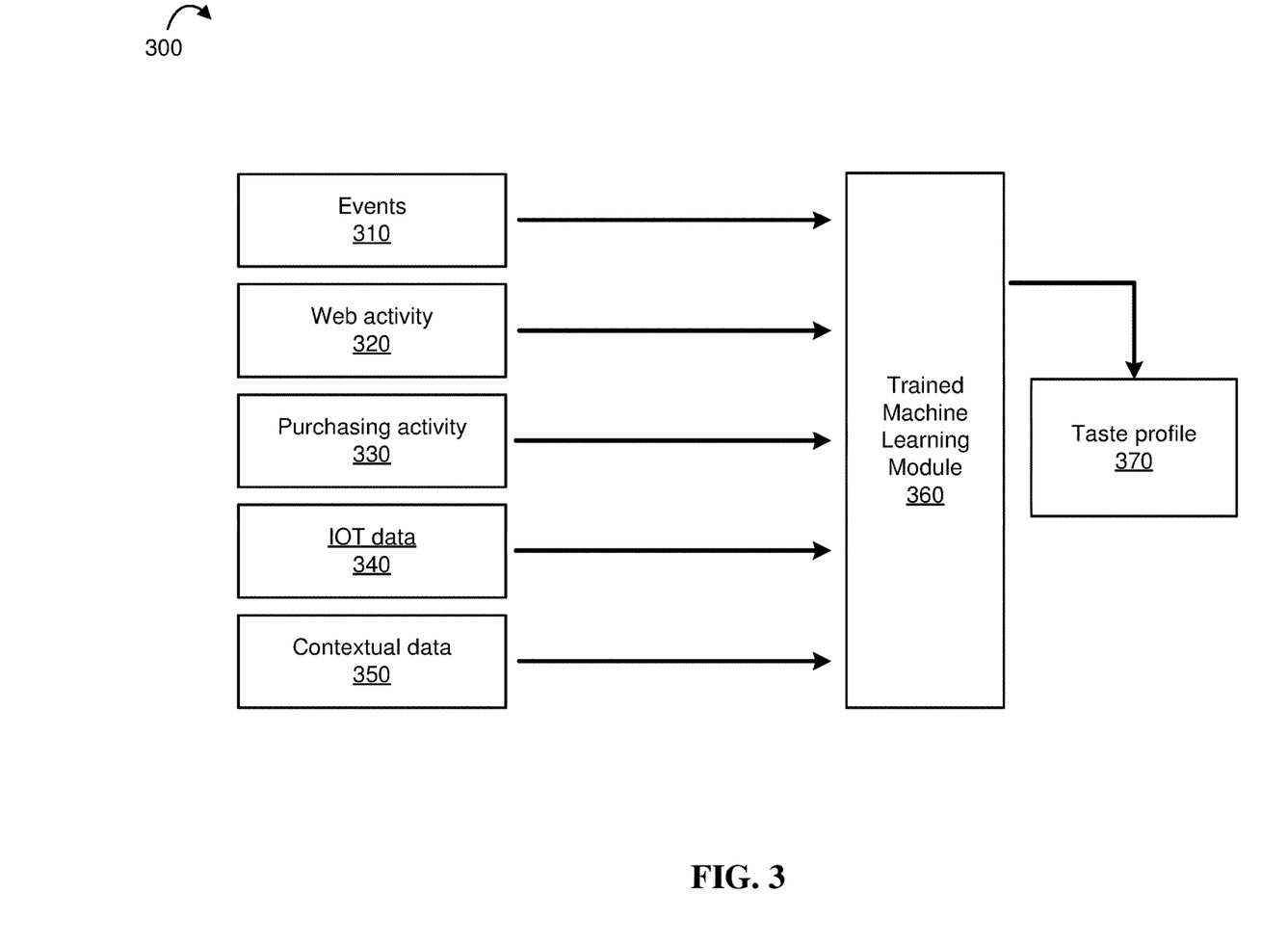
FIG. 3 depicts an example system block diagram of a trained machine learning module, in accordance with embodiments of the present disclosure.

FIG. 3 depicts an example system block diagram of a trained machine learning module that can be included in a taste profile system in accordance with embodiments of the present disclosure. Block diagram 300 includes an array of data that can be transmitted to a trained machine learning module 360. In some embodiments, the trained machine learning module 360 can be a processor that includes a machine learning algorithm configured to generate a taste profile 370 (e.g., a set of food items and/or a set of food characteristics that correspond to one or more food preferences of a user, such as the taste profile generated in step 230 discussed with respect to FIG. 2). In some embodiments, user feedback obtained by the taste profile system can be used to train the machine learning model.

Machine learning algorithms can include, but are not limited to, decision tree learning, association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques.

For example, the machine learning algorithms can utilize one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multidimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBRT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feed-forward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

In some embodiments, the array of data that can be input into the trained machine learning module 360 can include events 310 (e.g., calendar data); web activity 320 (e.g., user social media posts and user web browsing history); purchasing activity 330 (e.g., frequencies and/or quantities of purchased foods and/or food ingredients); IoT data 340 (e.g., camera images and/or audio recordings, information about quantities of food items and/or food ingredients obtained by smart refrigerators and smart containers); and contextual data 350 (e.g., menu information corresponding to a restaurant where the user is located and/or information regarding a time, date, season, location, and/or weather conditions corresponding to the user's dining activity). By using this array of data to generate a taste profile, embodiments of the present disclosure can account for a variety user activities that can indicate specific food preferences of the user. Accordingly, this array of data can allow the taste profile system to generate accurate food recommendations.

Figure 4:
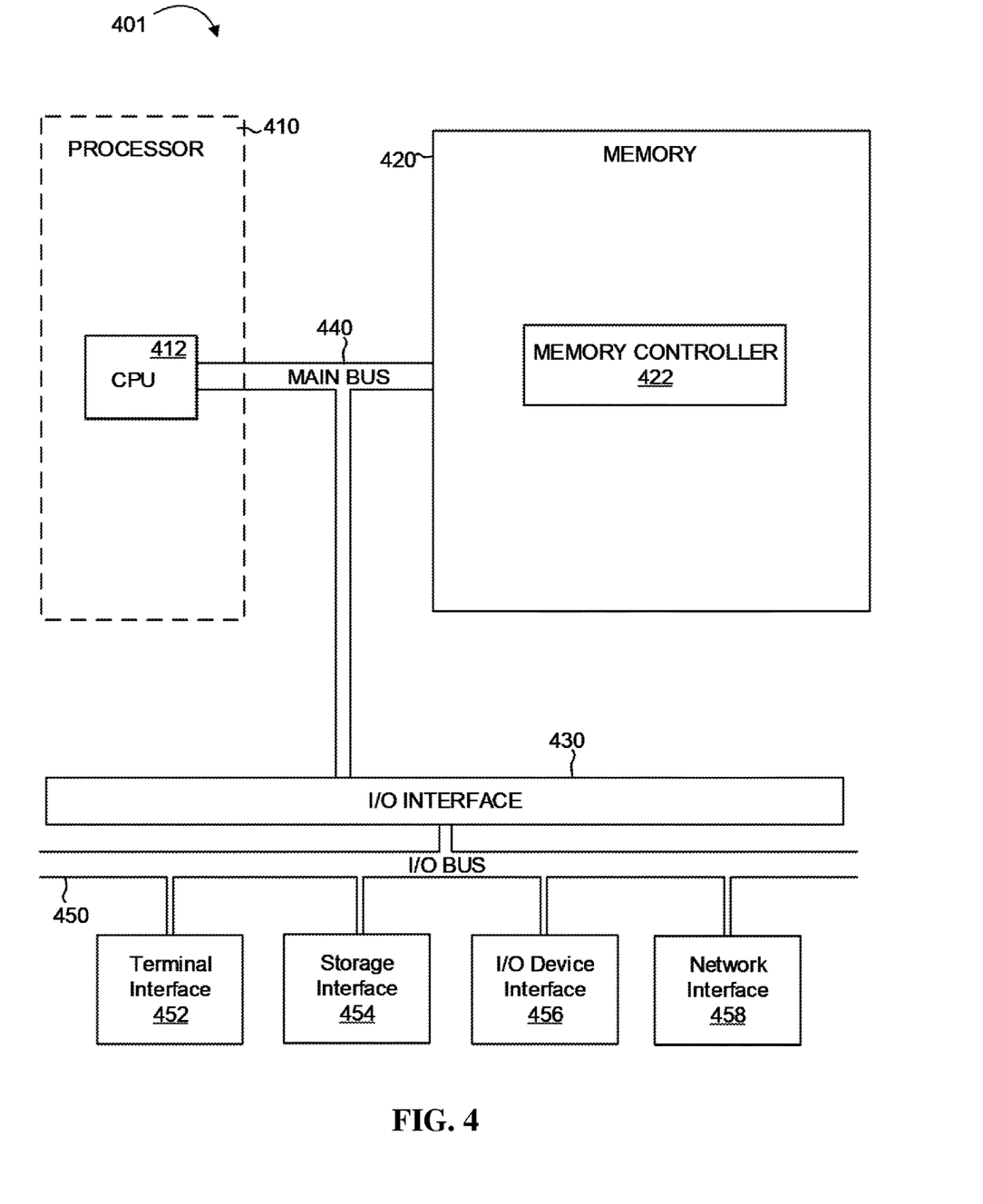
FIG. 4 depicts the representative major components of a computer system that can be used in accordance with embodiments of the present disclosure.

FIG. 4 depicts the representative major components of an exemplary Computer System 401 that can be used in accordance with embodiments of the present disclosure. The particular components depicted are presented for the purpose of example only and are not necessarily the only such variations. The Computer System 401 can comprise a Processor 410, Memory 420, an Input/Output Interface (also referred to herein as I/O or I/O Interface) 430, and a Main Bus 440. The Main Bus 440 can provide communication pathways for the other components of the Computer System 401. In some embodiments, the Main Bus 440 can connect to other components such as a specialized digital signal processor (not depicted).

The Processor 410 of the Computer System 401 can be comprised of one or more CPUs 412. The Processor 410 can additionally be comprised of one or more memory buffers or caches (not depicted) that provide temporary storage of instructions and data for the CPU 412. The CPU 412 can perform instructions on input provided from the caches or from the Memory 420 and output the result to caches or the Memory 420. The CPU 412 can be comprised of one or more circuits configured to perform one or methods consistent with embodiments of the present disclosure. In some embodiments, the Computer System 401 can contain multiple Processors 410 typical of a relatively large system. In other embodiments, however, the Computer System 401 can be a single processor with a singular CPU 412.

The Memory 420 of the Computer System 401 can be comprised of a Memory Controller 422 and one or more memory modules for temporarily or permanently storing data (not depicted). In some embodiments, the Memory 420 can comprise a random-access semiconductor memory, storage device, or storage medium (either volatile or non-volatile) for storing data and programs. The Memory Controller 422 can communicate with the Processor 410, facilitating storage and retrieval of information in the memory modules. The Memory Controller 422 can communicate with the I/O Interface 430, facilitating storage and retrieval of input or output in the memory modules. In some embodiments, the memory modules can be dual in-line memory modules.

The I/O Interface 430 can comprise an I/O Bus 450, a Terminal Interface 452, a Storage Interface 454, an I/O Device Interface 456, and a Network Interface 458. The I/O Interface 430 can connect the Main Bus 440 to the I/O Bus 450. The I/O Interface 430 can direct instructions and data from the Processor 410 and Memory 420 to the various interfaces of the I/O Bus 450. The I/O Interface 430 can also direct instructions and data from the various interfaces of the I/O Bus 450 to the Processor 410 and Memory 420. The various interfaces can comprise the Terminal Interface 452, the Storage Interface 454, the I/O Device Interface 456, and the Network Interface 458. In some embodiments, the various interfaces can comprise a subset of the aforementioned interfaces (e.g., an embedded computer system in an industrial application may not include the Terminal Interface 452 and the Storage Interface 454).

Logic modules throughout the Computer System 401—including but not limited to the Memory 420, the Processor 410, and the I/O Interface 430—can communicate failures and changes to one or more components to a hypervisor or operating system (not depicted). The hypervisor or the operating system can allocate the various resources available in the Computer System 401 and track the location of data in Memory 420 and of processes assigned to various CPUs 412. In embodiments that combine or rearrange elements, aspects of the logic modules' capabilities can be combined or redistributed. These variations would be apparent to one skilled in the art.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
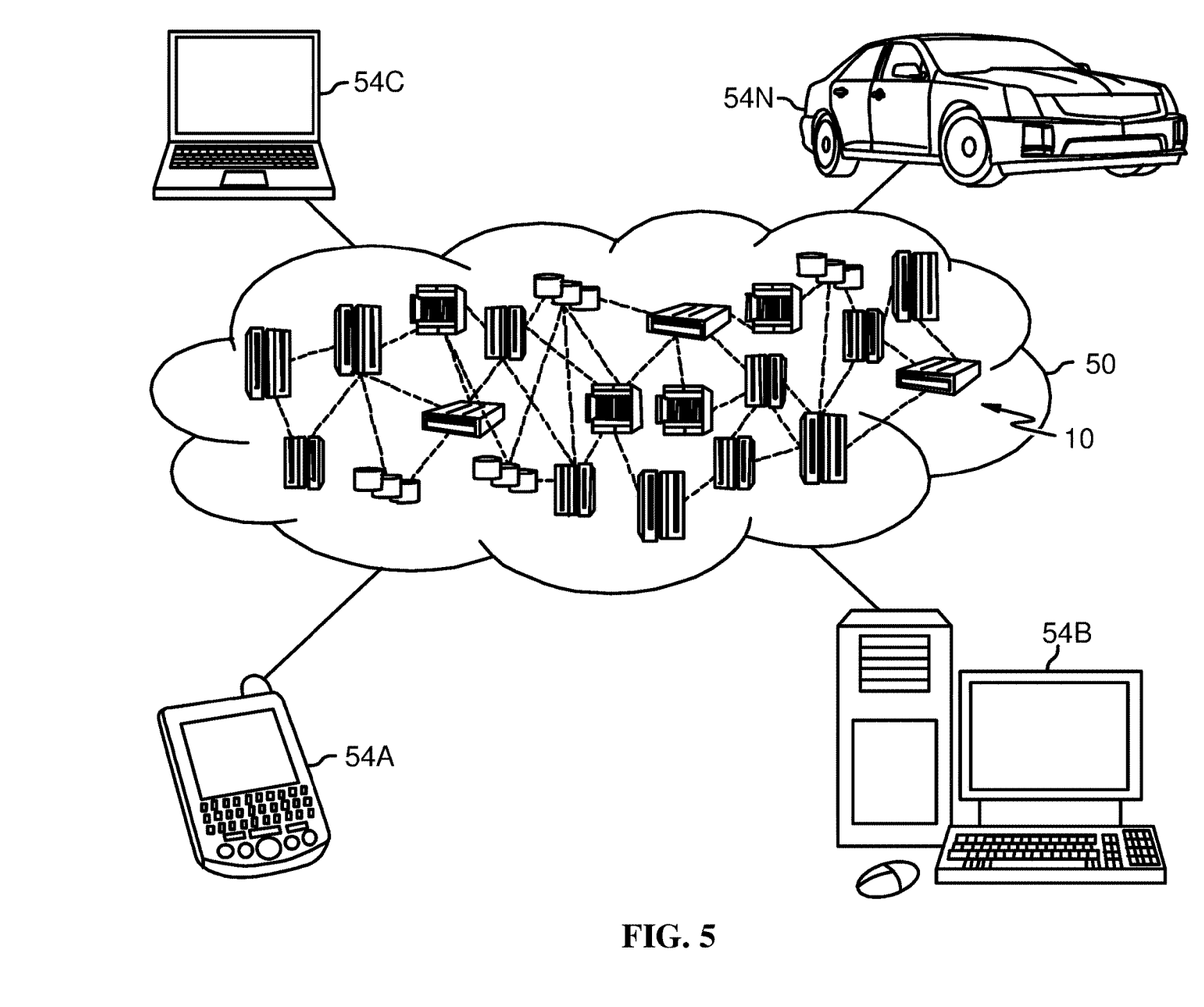
FIG. 5 depicts a cloud computing environment according to an embodiment of the present disclosure.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
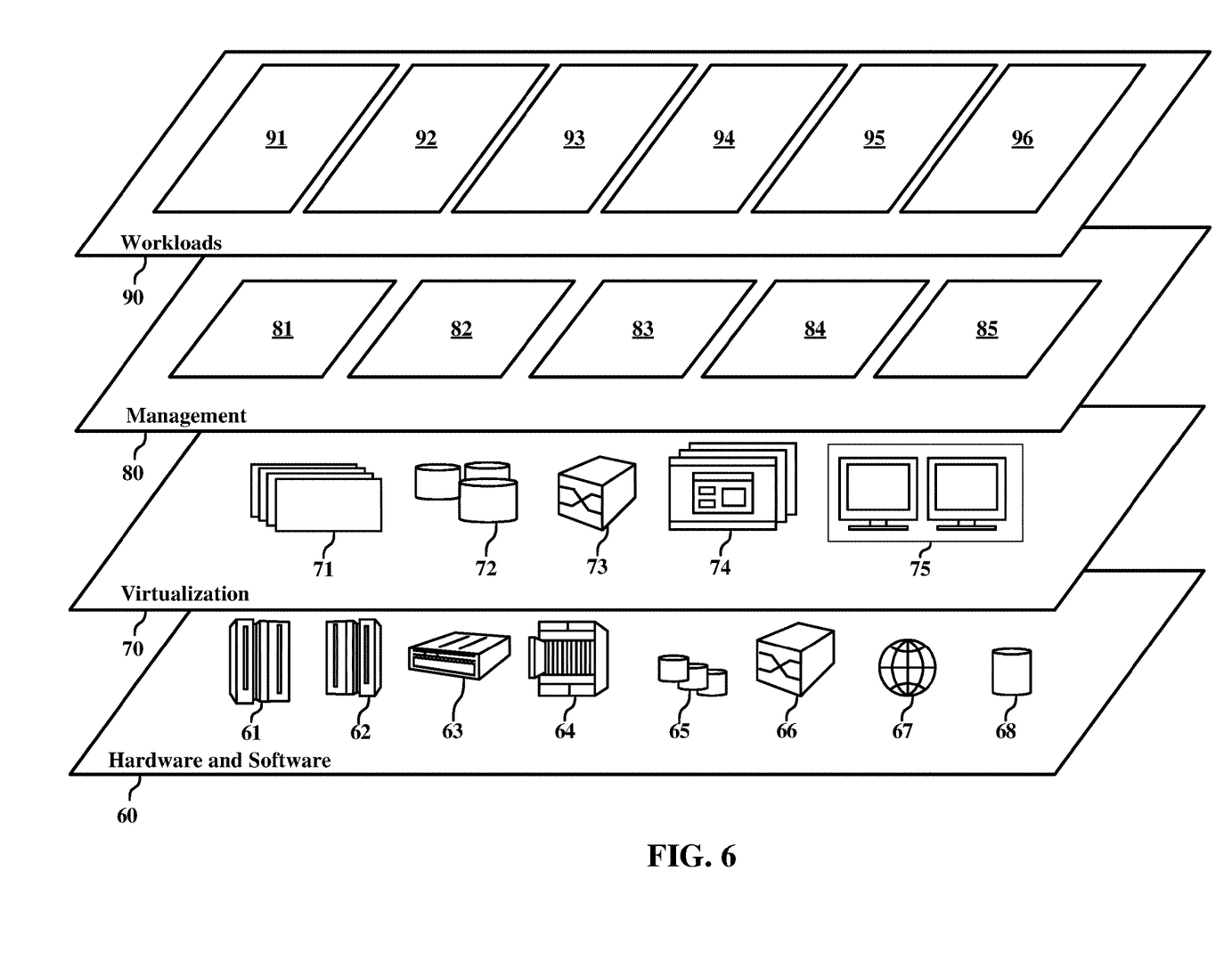
FIG. 6 depicts abstraction model layers according to an embodiment of the present disclosure.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and taste profile logic 96.

As discussed in more detail herein, it is contemplated that some or all of the operations of some of the embodiments of methods described herein can be performed in alternative orders or may not be performed at all; furthermore, multiple operations can occur at the same time or as an internal part of a larger process.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A computer-implemented method comprising:
    obtaining, by a camera, personal data of a user, the personal data comprising one or more images of the user preparing a food item, the one or more images comprising food ingredients utilized by the user;
    generating, by inputting the personal data into a trained machine learning module, a taste profile of the user, wherein the taste profile comprises a set of food characteristics that corresponds to one or more food preferences of the user;
    obtaining contextual data that corresponds to a location of the user;
    generating, based at least in part on the taste profile and the contextual data, a food recommendation, wherein the food recommendation includes a predicted food preference of the user; and
    transmitting the food recommendation to a user device.

2. The computer-implemented method of claim 1, wherein the food recommendation includes the food item.

3. The computer-implemented method of claim 1, wherein the personal data comprises a quantity of a food ingredient possessed by the user,
    and wherein the predicted food preference includes the food ingredient.

4. The computer-implemented method of claim 1, wherein the taste profile includes a home-cooked food item, and
    wherein the food recommendation includes a suggestion to cook the home-cooked food item.

5. The computer-implemented method of claim 1, wherein the taste profile includes a restaurant menu food item that is prepared at a restaurant, and
    wherein the predicted food preference includes the restaurant menu food item.

6. The computer-implemented method of claim 1, wherein generating the food recommendation comprises comparing the contextual data to the taste profile and identifying a match.

7. The computer-implemented method of claim 1, wherein the personal data of the user includes calendar data of the user, and
    wherein the food recommendation is based, at least in part, on the calendar data.

8. A system comprising:
    a processor; and
    a memory in communication with the processor, the memory containing program instructions that, when executed by the processor, are configured to cause the processor to perform a method, the method comprising:

obtaining, by a camera, personal data of a user, the personal data comprising one or more images of the user preparing a food item, the one or more images comprising food ingredients utilized by the user;

generating, by inputting the personal data into a trained machine learning module, a taste profile of the user, wherein the taste profile comprises a set of food characteristics that corresponds to one or more food preferences of the user;

obtaining contextual data that corresponds to a location of the user;

generating, based at least in part on the taste profile and the contextual data, a food recommendation, wherein the food recommendation includes a predicted food preference of the user; and transmitting the food recommendation to a user device.

9. The system of claim 8, wherein the food recommendation includes the food item.

10. The system of claim 8, wherein the personal data comprises a quantity of a food ingredient possessed by the user, and wherein the predicted food preference includes the food ingredient.

11. The system of claim 8, wherein the taste profile includes a home-cooked food item, and wherein the food recommendation includes a suggestion to cook the home-cooked food item.

12. The system of claim 8, wherein the taste profile includes a restaurant menu food item that is prepared at a restaurant, and wherein the predicted food preference includes the restaurant menu food item.

13. The system of claim 8, wherein generating the food recommendation comprises comparing the contextual data to the taste profile and identifying a match.

14. The system of claim 8, wherein the personal data of the user includes calendar data of the user, and wherein the food recommendation is based, at least in part, on the calendar data.

15. A computer program product comprising a computer readable storage medium having program instructions embodied therewith, wherein the computer readable storage medium is not a transitory signal per se, the program instructions executable by a processor to cause the processor to perform a method, the method comprising:

obtaining personal data of a user, the personal data comprising calendar data, web activity data, purchase history data, data from one or more Internet of Things (IoT) devices associated with the user, and one or more audio recordings of the user preparing the food item, obtained by a microphone;

generating, based at least in part on the personal data of the user, a taste profile of the user, the taste profile generated by inputting the personal data to a trained machine learning module and obtaining first weather information indicating weather conditions at a current time at a current location that is obtained from positional data of a global positioning system, wherein the taste profile comprises a set of food characteristics that corresponds to one or more food preferences of the user;

obtaining contextual data that corresponds to a location of the user and second weather information indicating weather conditions at a future time at a destination location that is obtained from navigational data of a navigation system;

generating, based at least in part on the taste profile and the contextual data, a food recommendation, the generating the food recommendation comprising comparing the contextual data to the taste profile and identifying a match, wherein the food recommendation includes a predicted food preference of the user; and transmitting the food recommendation to the user.

16. The computer program product of claim 15, wherein the personal data comprises one or more images of the user preparing a food item, and wherein the food recommendation includes the food item.

17. The computer program product of claim 15, further comprising:

obtaining, from a smart container or a smart refrigerator, the personal data comprising a quantity of a food ingredient possessed by the user, and wherein the predicted food preference includes the food ingredient.

18. The computer program product of claim 15, wherein the taste profile includes a home-cooked food item, and wherein the food recommendation includes a suggestion to cook the home-cooked food item.

19. The computer program product of claim 15, wherein the taste profile includes a restaurant menu food item that is prepared at a restaurant, and wherein the predicted food preference includes the restaurant menu food item.

20. The computer program product of claim 15, wherein the one or more audio recordings of the user preparing the food item, comprise food ingredients utilized by the user.

\* \* \* \* \*